United States Patent

Haehn

Patent Number: 5,336,839
Date of Patent: Aug. 9, 1994

[54] ABSORPTION COLUMN WITH EXTERNAL MIXING FOR ABSORPTION OF ACETYLENE

[75] Inventor: Peter-Clemens Haehn, Geretsried, Fed. Rep. of Germany

[73] Assignee: Linde Aktiengesellschaft, Wiesbaden, Fed. Rep. of Germany

[21] Appl. No.: 980,886

[22] Filed: Nov. 24, 1992

Related U.S. Application Data

[63] Continuation of Ser. No. 933,538, Aug. 24, 1992, abandoned.

[30] Foreign Application Priority Data

Aug. 23, 1991 [DE] Fed. Rep. of Germany ....... 4127987

[51] Int. Cl.$^5$ .................. C07C 7/10; B01D 19/00
[52] U.S. Cl. ........................ 585/833; 95/155
[58] Field of Search ............. 585/833; 55/63, 64

[56] References Cited

U.S. PATENT DOCUMENTS 4,655,798  4/1987  Ruch et al. .................... 55/64

Primary Examiner—Anthony McFarland
Assistant Examiner—Nhat D. Phan
Attorney, Agent, or Firm—Millen, White, Zelano & Branigan

[57] ABSTRACT

In the absorption of acetylene from a crude gas mixture containing mostly $C_2$ hydrocarbons by scrubbing with an absorbing agent, an externally produced mixture of about 10–70% by weight acetylene-free $C_2$ hydrocarbons and about 30–90% by weight absorption agent is introduced in the absorption column, in order to prevent the formation of foam. The mixture is produced in a static mixer outside the absorption column, and is supplied from outside the column to a mixing tank installed between two plates within the column.

17 Claims, 1 Drawing Sheet

ABSORPTION COLUMN WITH EXTERNAL MIXING FOR ABSORPTION OF ACETYLENE

CROSS-REFERENCE TO RELATED APPLICATION

This application is a continuation of application Ser. No. 07/933,538 filed Aug. 24 1992, now abandoned, and is related to a concurrently filed application, "Absorption Columns with Internal Mixing for Absorption of Acetylene", application Ser. No. 07/980,868, claiming priority of German application No. P 41 27 988.3, filed Aug. 23, 1991.

BACKGROUND OF THE INVENTION

This invention relates to a gas absorption process and apparatus, particularly for scrubbing acetylene out of a crude gas mixture containing mostly $C_2$ hydrocarbons.

The invention is especially directed to an improvement in the operation of a plate column, wherein the crude gas mixture is fed into the lower zone of the absorption column; fresh or regenerated absorption agent is fed to the upper zone of the absorption column; loaded absorption agent is drawn off the bottom of the absorption column and is fed to a regeneration stage; an acetylene-free product gas stream is withdrawn from the head of the absorption column, optionally after separation and recycling of a reflux condensate to the absorption column, and wherein a substantially acetylene-free liquid $C_2$ stream is introduced into the absorption column between the respective feed points for the crude gas mixture and the absorption agent.

In the extraction of ethylene from a thermally cracked cut of hydrocarbons, a crude gas mixture is obtained containing mostly $C_2$ hydrocarbons (ethylene, acetylene and optionally ethane). Besides the $C_2$ hydrocarbons, the crude gas mixture may also contain $C_3$ hydrocarbons and/or methane. Acetylene is conventionally removed from this crude gas mixture by scrubbing with an absorption agent selective for acetylene; however.

The absorption agent tends to foam under normal operating conditions, which results in downtime and/or acetylene escaping into the product gas.

The formation of both hydrocarbon-rich and hydrocarbon-poor liquid phases, in addition to the vapor phase, are generally responsible for the foam. These two liquid phases are formed when the saturation limit of the absorption agent is exceeded relative to the hydrocarbons present. But foam formation can also occur far below the saturation limit in the absorption column, particularly under unstable operating conditions.

In this connection, EP-B 158 280, corresponding to U.S. Pat. No. 4,665,798, describes a process intended to prevent foam formation by providing an additional feed of a substantially acetylene-free liquid $C_2$ stream into the absorption column. From DE-OS 38 33 795, another process is known wherein the gaseous stream withdrawn from the head of the absorption column, is partially condensed and is recycled into the absorption column and a branched partial stream of the reflux condensate is introduced in the absorption column between the feed points for the crude gas mixture and for the absorption agent. Both of these processes, however, do not solve the problem of foam formation entirely satisfactorily.

SUMMARY OF THE INVENTION

An object of this invention, therefore, is to provide a process and apparatus leading to a diminution or complete prevention of foam formation.

Upon further study of the specification and appended claims, further objects and advantages of this invention will become apparent to those skilled in the art.

These objects are achieved according to the invention by mixing, at a location externally of the column: (a) a substantially acetylene-free liquid $C_2$ stream and/or said partial stream of the reflux condensate with (b) the absorption agent, and introducing the resultant mixture into the absorption column.

For the process according to the invention, all absorption agents are suitable which exhibit a selective solubilizing power relative to acetylene, such as, for example, N-methylpyrrolidone (NMP) or dimethylformamide (DMF).

The crude gas mixture containing mostly $C_2$ hydrocarbon generally contains on a percent by volume basis about 0.5 to about 4.0 acetylene and about 95.0 to about 99.0 other $C_2$ hydrocarbons.

The substantially acetylene-free liquid $C_2$ stream generally contains in percent by weight basis, less than about 5 ppm, especially less than about 0.5 ppm, acetylene.

The composition of the partial stream of the reflux condensate is generally in principle identical with the composition of the overhead product stream.

The temperature and pressure conditions in the column are generally about 210 to 283, preferably 238° to 273° K. and about 6.0 to 30.0, preferably 15.0 to 30.0 bar.

Surprisingly, it has been shown that a foam formation can be prevented by external mixing outside the absorption column and the introduction of the mixture in the absorption column. In addition, the consumption of resources can be lowered by the process according to the invention because of the evaporation of the $C_2$-hydrocarbons. The evaporation of the $C_2$-hydrocarbons contributes to a decreasing of the absorption temperature in the column and consequently the temperature of the absorption agent drops. As a result, the solubilizing power of the absorption agent is further increased relative to the acetylene. The increasing of the solubilizing power of the absorption agent leads to a decreasing of the required amount of absorption agent in the column, respectively, the scrubbing process. Further, an advantageous operation of the absorption process in the column is assured due to the following facts: reducing the absorption temperature, minimizing the foaming risk and decreasing the additional ethylene absorption because of the reduced amount of absorption agent.

Besides the addition of the mixture into the absorption column according to the invention, a partial stream of the reflux condensate and/or a substantially acetylene-free $C_2$ stream can also be fed into the absorption column. Also, reflux condensate is optionally but preferably passed into the head of the absorption column, but in this case, it is preferred to dispense with any addition of unmixed feed of a partial stream of the reflux condensate or a substantially acetylene-free $C_2$ stream to the absorption column.

The mixing of the $C_2$ stream and the absorption agent advantageously is performed preferably in a static mixer outside the absorption column. In this way, a homogeneous mixture can be obtained. By "static mixer" is meant a mixer without any agitating or moving parts. In principle, a dynamic mixer, e.g., a tank with an agitator, can also be used.

In further development of the process according to the invention, the absorption agent in the column accumulates in a zone located between two plates, and the mixture is injected into this zone, hereinafter referred to as "internal mixing zone". Thus, there is obtained an immediate and thorough mixing of the mixture with the absorption agent within the absorption column. The mixture is preferably introduced into the absorption column between the respective feed points for the crude gas mixture and the absorption agent, and it is especially preferred for the mixture to be introduced into the lower third of the absorption column.

In a still further development of the invention, the externally produced mixture preferably has a temperature which is below the temperature of the absorption agent in the column, into which the mixture is introduced. In this way, the absorption agent in the absorption column can be subcooled, resulting in an increase in the solubilizing power of the absorption agent relative to acetylene.

For example, it is preferred that the temperature of the externally produced mixture is about 1° to 20°, preferably 2° to 15° below the temperature of the absorption agent in the column.

The mixture can also be split into a plurality of streams and passed into the absorption column at different locations and with different temperatures so as to control the temperature profile in the scrubbing column.

In a further embodiment of the invention, the internal mixing zone and the plate downcomers, which are between the individual plates can be filled with packing, e.g., structured or non-structured packing. In this way, on the one hand, the gas-liquid contact is more efficient, and on the other hand, the mixing of the liquids is improved.

According to the invention, the mixture contains between 10 and 70% by weight, preferably between 30 and 50% by weight of the substantially acetylene-free $C_2$ hydrocarbons, the remainder being the absorption agent.

In the apparatus aspect of the invention, there is provided an absorption column having a plurality of plates, a feed pipe for the crude gas mixture, a feed pipe for the regenerated absorption agent, an outlet for the acetylene-free product gas stream, an outlet for the loaded absorption agent, and optionally a feed pipe for a partial stream of the reflux condensate.

According to the invention, an internal mixing tank open on top is installed between two plates and a feed pipe for the mixture leads into or above said tank. The feed pipe is directly or indirectly connected to mixing means outside of the column for mixing substantially acetylene-free liquid $C_2$ stream and/or the partial stream of the reflux condensate with the absorption agent.

The feed pipe of the mixture can be branched into a plurality of pipe ends in the mixing tank. In this way, a better distribution of the mixture in the pool of absorption agent can be obtained. Advantageously, the feed pipes of the mixture in the mixing tank and/or the pipe ends are also provided with outlet orifices preferably on their top side. The outlet orifices produce a finely divided addition of the mixture in the absorbing agent.

In still further development of the invention, a static mixer is incorporated in the feed pipe for the mixture outside the absorption column. The static mixer produces a homogeneous mixture of $C_2$ hydrocarbons and absorbing agent.

BRIEF DESCRIPTION OF THE DRAWING

Various other objects, features and attendant advantages of the present invention will be more fully appreciated as the same becomes better understood when considered in conjunction with the accompanying drawing, in which like reference characters designate the same or similar parts throughout the several views, and wherein.

DETAILED DESCRIPTION OF THE DRAWING

Figure 1:
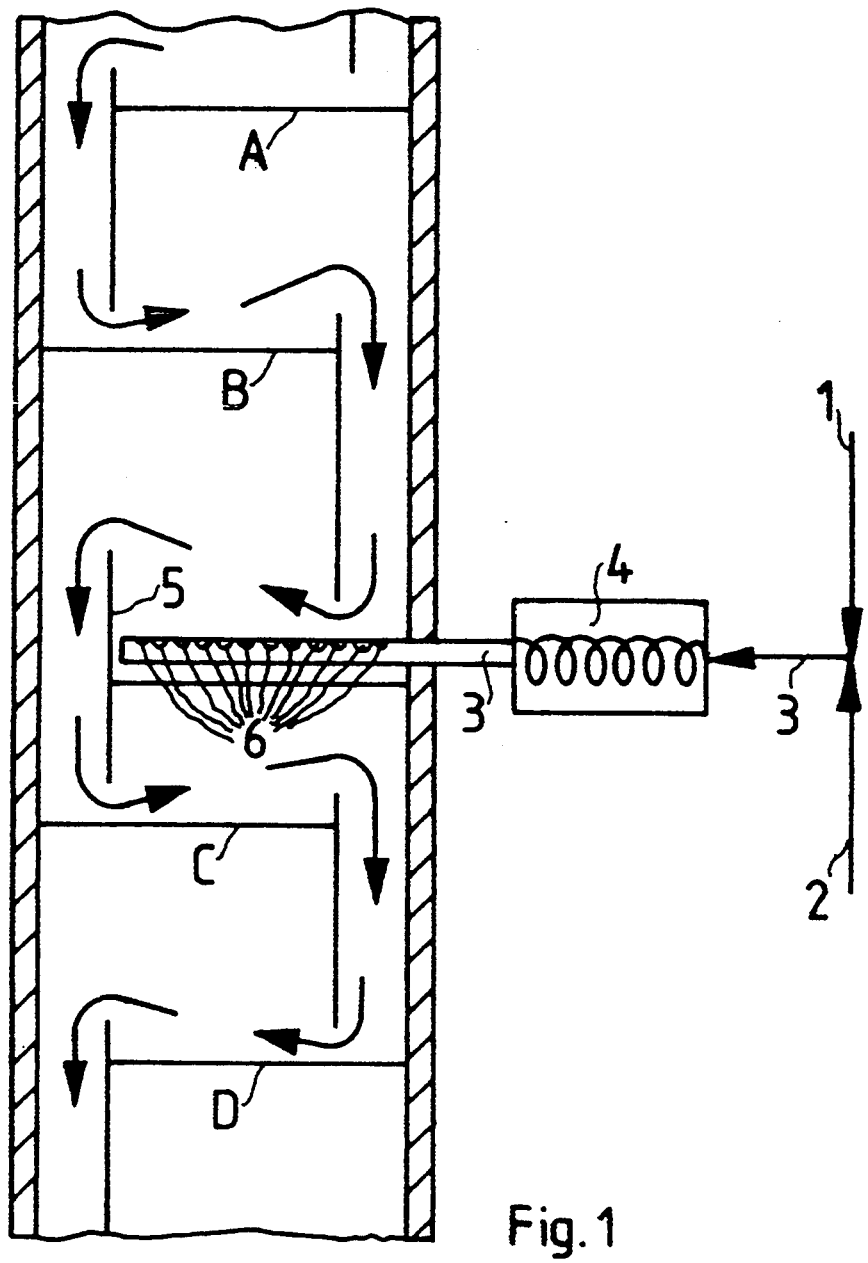
FIG. 1 is a front vertical schematic view of an absorption column according to the invention.

In FIG. 1, the cutaway portion illustrates plates A, B, C and D, for which, for example, may be bubble cap plates or sieve plates. Offset downcomers are installed in the absorption column between the plates. The absorption agent falls countercurrently to the rising gas from one plate to the underneath plates by the associated plate downcomer. The direction of the absorption agent flowing downward in the absorption column is represented by arrows.

A substantially acetylene-free $C_2$ stream in the liquid phase under a pressure of about 0.1 to 1 bar above the column pressure at the inlet point of the mixture, and about a temperature of about $-10°$ to $-55°$ C., depending on the pressure, in pipe 1 is joined together with absorption agent from pipe 2 and the mixture is passed into pipe 3. The absorption agent in pipe 2 is branched, for example, from regenerated absorbing agent recycled to the absorption column. The absorption agent is generally at a temperature of about 1° to 15°, preferably 2° to 11° above the temperature of the crude gas stream, and is present under sufficiently high pressure to be mixed with the $C_2$ stream.

The mixture of $C_2$ hydrocarbons and absorption agent in pipe 3 is homogeneously mixed in an external static mixer 4 which is a mixer with static fittings, e.g., a spiral coil.

From the static mixture, the mixture is passed by pipe 3 into internal mixing tank 5. Mixing tank 5 is associated with a downcomer installed between trays B and C. Feed pipe 3 is provided with outlet openings inside the mixing tank on its top side, by which the mixture is introduced in finely divided droplets into the absorption agent accumulated in the mixing tank. By virtue of a lower temperature of the mixture, it subcools the absorption agent in the mixing tank 5. The liquid absorption agent is passed from mixing tank 5, open on top, by the downcomer of mixing tank 5 between plates B and C to tray C, to the plates below.

The invention can suitably be used in the absorption of all acetylenes from hydrocarbon streams, for example, in the removal of methyl acetylene from a $C_3$ stream.

It is also contemplated that this invention will be useful in any gas absorption column, in order to prevent foaming.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 41 27 987.5, filed Aug. 23, 1991, are hereby incorporated by reference.

EXAMPLE

A crude gas stream with a temperature of 225.0° K. and pressure of 10.0 bars containing

| 1.0 vol. % | $C_2H_2$ |
| 84.0 vol. % | $C_2H_4$ |
| 14.0 vol. % | $C_2H_6$ and |
| 1.0 vol. % | $C_{3+}$ | is fed into the lower zone of the absorption column. A regenerated DMF stream as absorption agent is introduced into the upper zone of the absorption column with a temperature of 238.0° K. and a pressure of 10.2 bars. Loaded DMF is withdrawn from the bottom of the absorption column with a temperature of 243.0° K. and a pressure of 10.3 bars. An acetylene-free product gas stream containing

| $C_2H_2$ | <1 ppm |
| $C_2H_4$ | 85.7 vol. % |
| $C_2H_6$ | 14.3 vol. % | is withdrawn with a temperature of 223.0° K. and a pressure of 10.0 bars from the head of the absorption column. A reflux condensate of the overhead product gas stream with a temperature of 223.0° K. and a pressure of 10.5 bars is passed to the head of the absorption column.

According to the invention, a partial stream of the reflux condensate with a temperature of 223.0° K. and a pressure of 10.5 bars is mixed outside the absorption column with a DMF stream with a temperature of 238.0° K. and a pressure of 10.5 bars. After mixing thoroughly the acetylene-free $C_2$ stream (in this example the partial stream of the reflux condensate) and the DMF stream in a static mixer the resultant mixture is introduced in the mixing tank of the absorption column. Alternatively, an external liquid acetylene-free $C_2$ stream can be used instead of the partial stream of reflux condensate. Such an external substantially acetylene-free $C_2$ stream can be, for example, pure ethylene, e.g., from a $C_2$ cycle of the petrochemical plant. An external substantially acetylene-free liquid $C_2$ stream must be used in the case of no leading back a reflux stream to the head of the absorption column.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for removing acetylene from a crude gas mixture containing mostly $C_2$ hydrocarbons by scrubbing with an absorption agent in a plate absorption column having a head and a bottom wherein the crude gas mixture is fed into a lower zone of the absorption column; fresh or regenerated absorption agent is fed into an upper zone of the absorption column, loaded absorption agent is withdrawn from the bottom of the absorption column and is fed to a regeneration stage, and an acetylene-free product gas stream is withdrawn from the head of the absorption column, the improvement comprising mixing absorption agent, a substantially acetylene-free liquid $C_2$ stream and/or a partial stream of reflux condensate outside the absorption column, and passing resultant mixture into the absorption column, thereby diminishing foam formation.

2. A process according to claim 1, wherein the absorption agent, the substantially acetylene-free liquid $C_2$ stream and/or the partial stream of reflux condensate are mixed in a static mixer outside the absorption column.

3. A process according to claim 1, wherein the resultant mixture is introduced into a pool of absorption agent within the column, said pool lying in an internal mixing zone located between two superposed plates in the absorption column.

4. A process according to claim 1, wherein the resultant mixture is passed into the absorption column at a point between where the crude gas mixture is fed into the column and where the fresh or regenerated absorption agent is fed into the column. absorption column between respective feed points for the crude gas mixture and the fresh or regenerated absorption agent.

5. A process according to claim 1, wherein the resultant mixture is introduced into the lower third of the absorption column.

6. A process according to claim 3, wherein the resultant mixture has a temperature below the temperature of the absorption agent into which the mixture is introduced.

7. A process according to claim 3, wherein the internal mixing zone and a downcomer associated therewith are filled with packing.

8. A process according to claim 1, wherein the resultant mixture consists essentially of 10 to 70% by weight of substantially acetylene-free $C_2$ hydrocarbons.

9. A process according to claim 1, wherein the resultant mixture consists essentially of 30 to 50% by weight of substantially acetylene-free $C_2$ hydrocarbons.

10. A process according to claim 1, wherein said partial stream of reflux condensate is mixed with the absorption agent outside the absorption column.

11. A process according to claim 1, wherein a partial stream of reflux condensate is passed to the head of the absorption column and remaining reflux condensate is mixed with the absorption agent outside the column.

12. A process according to claim 3, wherein the resultant mixture is passed into the absorption column at a point between where the crude gas mixture is fed into the column and where the fresh or regenerated absorption agent is fed into the column.

13. A process according to claim 10, wherein the resultant mixture is passed into the absorption column at a point between where the crude gas mixture is fed into the column and where the fresh or regenerated absorption agent is fed into the column.

14. A process according to claim 11, wherein the resultant mixture is passed into the absorption column at a point between where the crude gas mixture is fed into the column and where the fresh or regenerated absorption agent is fed into the column.

15. A process according to claim 6, wherein the temperature difference is 1°–20° C.

16. A process according to claim 6, wherein the temperature difference is 2°–15° C.

17. A process according to claim 1, wherein the absorption agent is N-methylpyrrolidone or dimethylformamide.

* * * * *

UNITED STATES PATENT AND TRADEMARK OFFICE
CERTIFICATE OF CORRECTION

PATENT NO. : 5,336,839
DATED : August 9, 1994
INVENTOR(S) : Peter-Clemens HAEHN

It is certified that error appears in the above-indentified patent and that said Letters Patent is hereby corrected as shown below:

In claim 4, column 6, lines 31-33: After "column", delete the remainder of the claim.

Signed and Sealed this

Sixth Day of December, 1994

Attest:

BRUCE LEHMAN

Attesting Officer

Commissioner of Patents and Trademarks